United States Patent [19]
deBoisblanc et al.

[11] Patent Number: 6,113,548
[45] Date of Patent: Sep. 5, 2000

[54] METHOD AND APPARATUS FOR ESTIMATION OF BEAT-TO-BEAT PULMONARY WEDGE PRESSURE

[76] Inventors: Bennet P. deBoisblanc, 27 Herron St., New Orleans, La. 70124; Royce W. Johnson, 114 Rimdale, Universal City, Tex. 78148; Andy Pellett, 1105 Focis St., Metairie, La. 70005; Glenn B. Bell, 3454 Tyler Ct., Ellicott City, Md. 21042

[21] Appl. No.: 09/371,326

[22] Filed: Aug. 10, 1999

Related U.S. Application Data

[63] Continuation of application No. PCT/US98/02807, Feb. 11, 1998.
[60] Provisional application No. 60/037,676, Feb. 11, 1997.

[51] Int. Cl.$^7$ ............................................. A61B 5/02
[52] U.S. Cl. ................................. 600/485; 600/500
[58] Field of Search .................... 600/485–488, 600/500

[56] References Cited

U.S. PATENT DOCUMENTS

| | | | |
|---|---|---|---|
| 4,856,529 | 8/1989 | Segal | 128/661.08 |
| 4,869,263 | 9/1989 | Segal et al. | 128/692 |
| 5,046,505 | 9/1991 | Sekii et al. | 600/326 |
| 5,423,323 | 6/1995 | Orth | 128/673 |

*Primary Examiner*—Cary O'Connor
*Assistant Examiner*—Ryan Carter
*Attorney, Agent, or Firm*—Wayne J. Colton, Inc.

[57] ABSTRACT

A medical device for estimation of pulmonary wedge pressure wherein a non-occluded pulmonary artery blood pressure measurement is utilized to directly estimate the pulmonary wedge pressure. A neural network is trained with occlusion-obtained data, whereafter the trained coefficients are utilized to implement the wedge pressure estimator. A flow-directed catheter is utilized to transduce the pressure waveform, which is then input to the processing computer through a analog-to-digital data acquisition board. The data is preprocessed in the computer in order to present the neural network with 11 samples of blood pressure data and 11 samples of time-correlated first derivatives of the blood pressure data as well as an indication of the length in time of the heartbeat. The trained neural network then directly outputs the estimated wedge pressure.

9 Claims, 3 Drawing Sheets

METHOD AND APPARATUS FOR ESTIMATION OF BEAT-TO-BEAT PULMONARY WEDGE PRESSURE

RELATED APPLICATION

This application is a continuation of PCT international application No. PCT/US98/02807 filed Feb. 11, 1998, which claims priority to U.S. provisional application Serial No. 60/037,676 entitled METHOD AND APPARATUS FOR ESTIMATION OF PULMONARY CAPILLARY AND WEDGE PRESSURES filed Feb. 11, 1997 by the same inventors. By this reference, the full disclosures, including the drawings, of PCT international application No. PCT/US98/02807 and U.S. provisional application Serial No. 60/037,676 are incorporated herein.

FIELD OF THE INVENTION

The present invention relates to cardiopulmonary diagnostics. More specifically, the present invention relates to a method and apparatus by which beat-to-beat pulmonary wedge pressure may be obtained without necessity for the hazardous inflation of a pulmonary artery catheter balloon.

BACKGROUND OF THE INVENTION

Pulmonary wedge pressure, also sometimes referred to as pulmonary occlusion pressure, is an estimate of the left atrial, or left heart filling, pressure. The pulmonary wedge pressure has been widely used by clinicians as a valuable indication of a patient's cardiac output performance, and is especially useful during post-operative pharmaceutical and/or fluid titration in cardiovascular surgery patients. Under the current state of the art, wedge pressure is obtained by inserting a balloon flotation catheter, such as the well-known Swan-Ganz type flow-directed catheter, through the heart and into a smaller branch of the pulmonary artery. Once the catheter is in place, a balloon at the distal tip of the catheter is inflated to occlude blood flow through the branch. The pressure within the branch distal the occlusion, which is measured by a sensor in or near the tip of the catheter and distal the balloon, will then decay to some stable baseline value representative of the left heart filling pressure. The change over time of this filling pressure is then used by the clinician to judge the improvement, or lack thereof, in the patient's cardiac output.

Unfortunately, the conventional method for obtaining wedge pressure presents significant risk to the patient. Inflation of the catheter's balloon within the pulmonary artery causes a distinct force to be exerted outwardly against the artery's interior wall. A naturally fragile or otherwise weakened artery may not tolerate this outward force, resulting in rupture of the artery. Although not extraordinarily common, the ultimate effect of a ruptured artery is catastrophic to the patient; a surgical team has only between about 30 seconds and three minutes to open the patient's chest and clamp the bleeder before the patient bleeds to death into the plural cavity. To compound the problem, pulmonary artery catheters have a tendency to migrate downstream. As the catheter enters smaller and smaller portions of the arterial branch, the chance for rupture of the artery increases. Because of these inherent risks, the clinician's need for repeated wedge pressure measurements must be weighed against the jeopardy in which the patient is placed to obtain each and every measurement. The end result is a tendency to not often repeat the measurement except in the most acute cases, wherein the measurement is still only taken about every fifteen minutes. Because the greatest value for the pulmonary wedge pressure is derived from analysis of how the wedge pressure changes over time, the inability to obtain frequently repeated measurements presents a serious clinical limitation.

It is therefore a specific object of the present invention to obtain an estimate of the pulmonary wedge pressure without need for inflation of a pulmonary artery catheter balloon. It is a further object of the present invention to obtain such a measure, utilizing the beat-to-beat pulmonary artery blood pressure waveform, on a beat-by-beat basis in order to provide a more clinically useful indication of the dynamic aspects of a patient's cardiac condition. It is yet a further object of the present invention to provide an analysis machine for converting the pulmonary artery blood pressure waveform into the desired beat-by-beat estimate of pulmonary wedge, or occlusion, pressure.

SUMMARY OF THE INVENTION

In accordance with the foregoing objects, the present invention generally comprises a medical device for estimation of pulmonary wedge pressure wherein a non-occluded pulmonary artery blood pressure measurement is utilized to directly estimate the pulmonary wedge pressure. According to the preferred embodiment of the invention, a neural network is trained with occlusion-obtained data, whereafter the trained coefficients are utilized to implement the wedge pressure estimator. In at least one embodiment, a flow-directed catheter is utilized to transduce the pressure waveform, which is then input to the processing computer through a analog-to-digital data acquisition board. The data is preprocessed in the computer in order to present the neural network with 11 samples of blood pressure data and 11 samples of time-correlated first derivatives of the blood pressure data as well as an indication of the length in time of the heartbeat. The trained neural network then directly outputs the estimated wedge pressure.

Many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein:

FIG. 4 shows, in flowchart, operation of the implemented invention.

DETAILED DESCRIPTION OF THE PREFERRED EMBODIMENT

Figure 1:
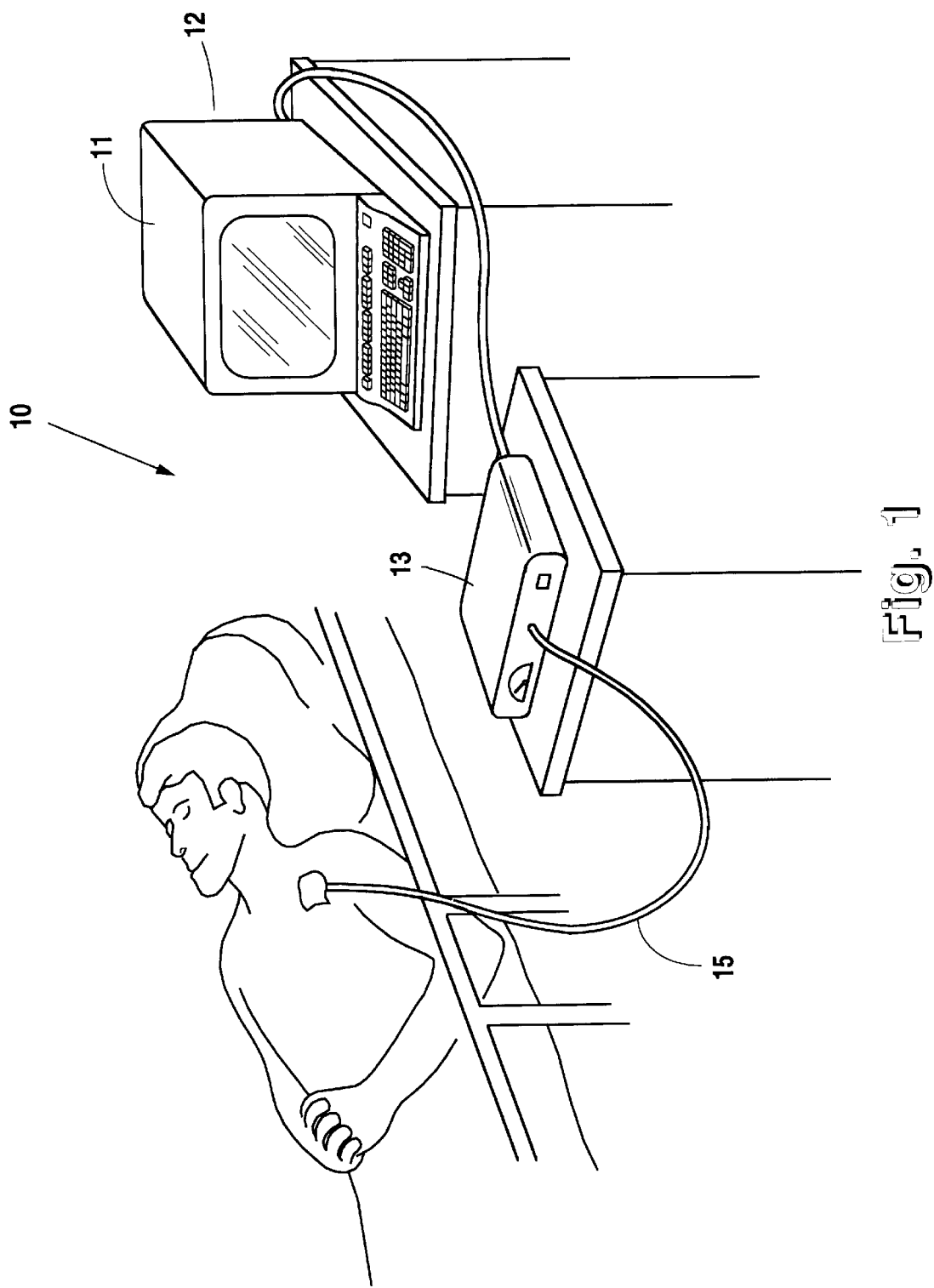
FIG. 1 shows, in perspective overview, the present invention as placed in use with a patient.
Figure 2:
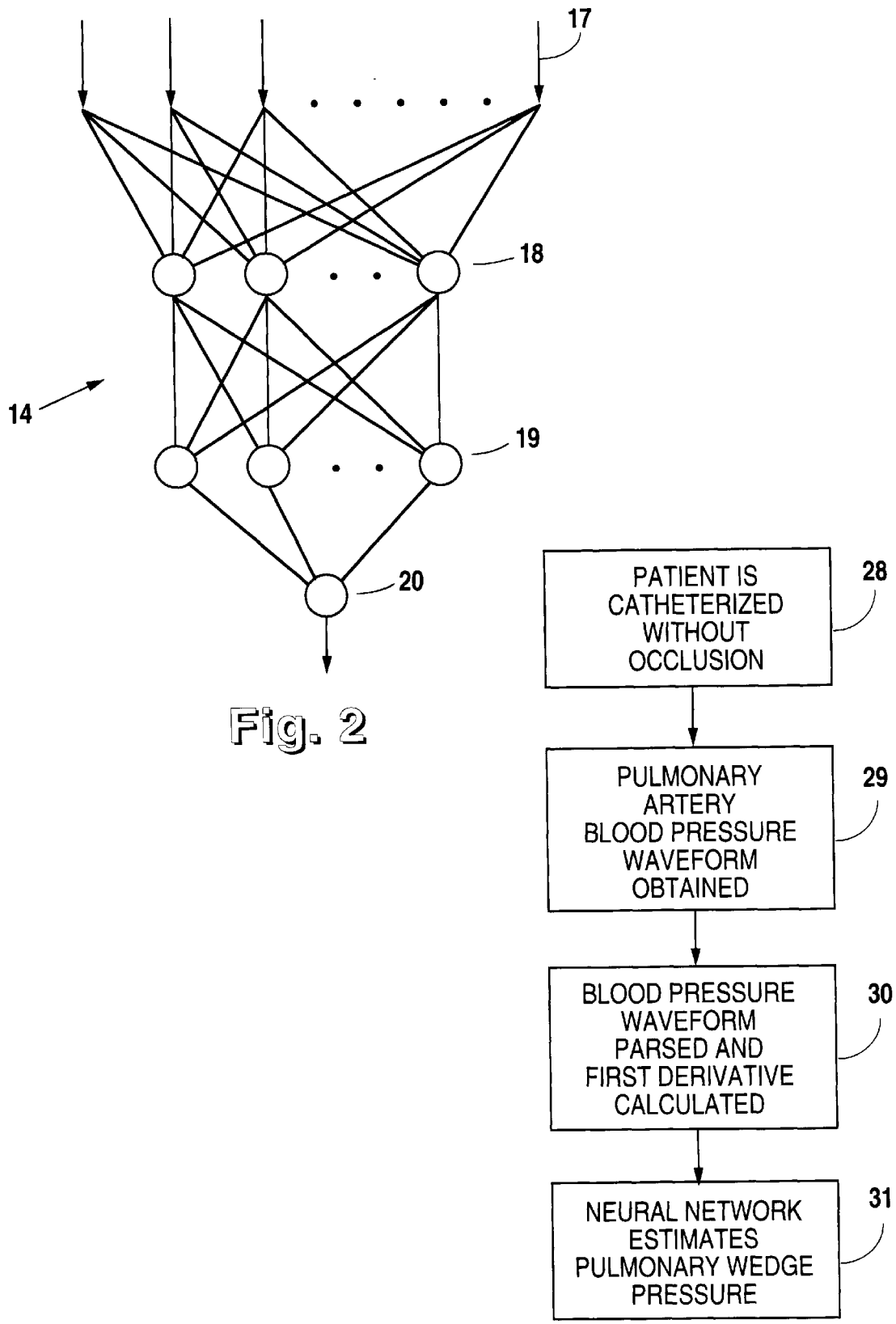
FIG. 2 shows, in block diagram, a back-propagation neural network as is appropriate for implementation of the present invention.
Figure 3:
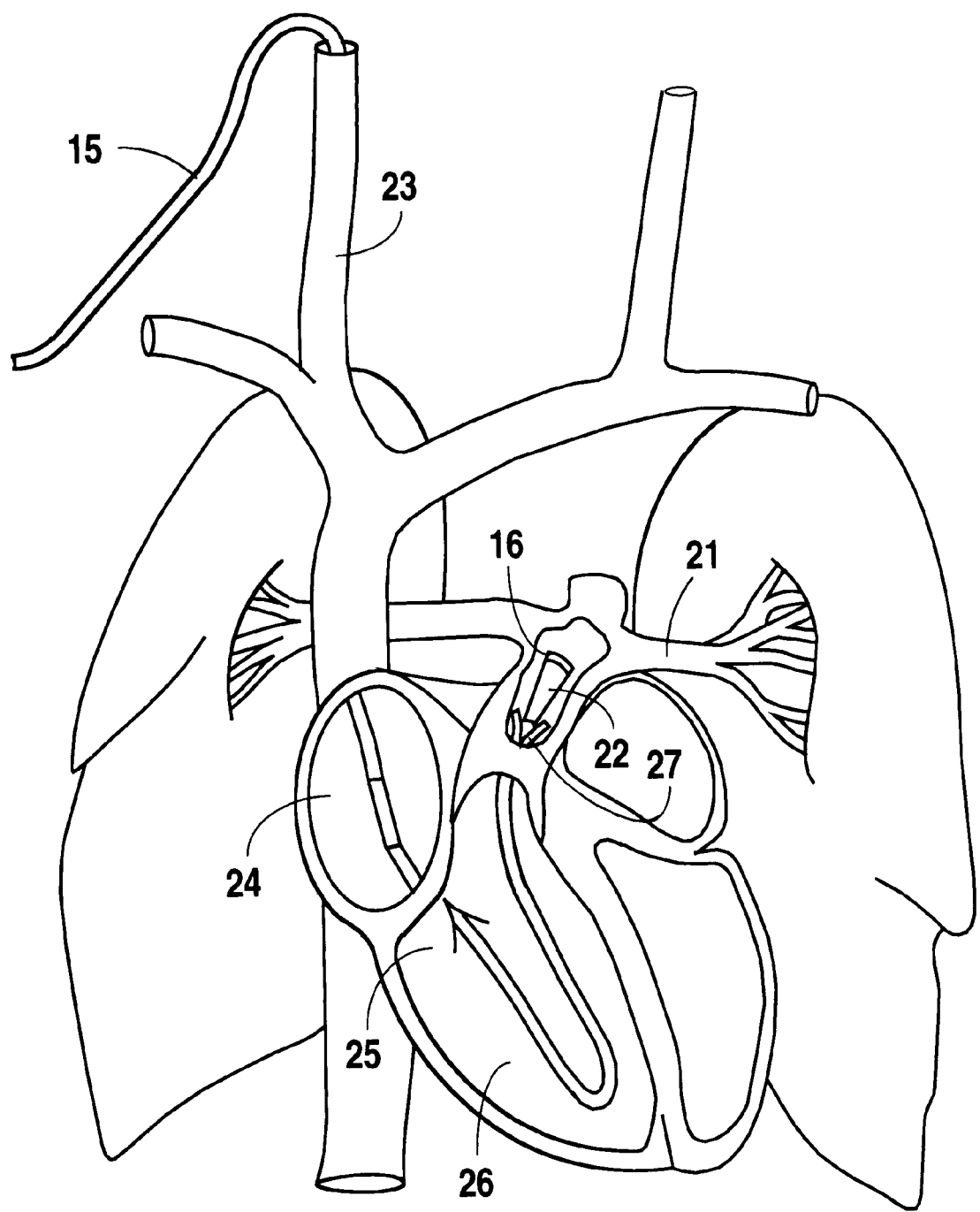
FIG. 3 shows, in cut view, placement of a flow-directed catheter in a human cardiovascular system.

Although those of ordinary skill in the art will readily recognize many alternative embodiments, especially in light of the illustrations provided herein, this detailed description is exemplary of the preferred embodiment of the present invention—a method and apparatus for estimation of pulmonary wedge pressure 10, the scope of which is limited only be the claims appended hereto. In the preferred embodiment, the present invention generally comprises an Apple Macintosh trademark POWERMAC model 8100 with 48 Megabytes internal RAM 11, commercially available from Apple Computers of Cupertino, California and/or its many known distributors; a model NB-AIO-16 12 bit, 16 channel analog to digital data acquisition board 12 under software control of trademark LABVIEW for Macintosh data acquisition software, each commercially available from National Instruments of Austin, Texas and/or its many known distributors; a data preprocessing and neural network implementation 14; and a pulmonary artery blood pressure measurement device 13.

As will be better understood further herein, the preferred embodiment of the present invention utilizes the well-known backward error propagation neural network architecture 14. Those of ordinary skill in the art will recognize, however, that many other architectures may equivalently be implemented, including, but not limited to, quick-propagation, radial basis function, modular and generalized genetic networks. As also will be better understood further herein, the preferred embodiment utilizes a flow-directional catheter 15 equipped at the tip with a stain gauge pressure transducer 16 for measuring the pressure waveform within the pulmonary artery. While the use of a flow-directed pulmonary artery catheter is very convenient for developing the wedge pressure estimator, it is not necessary for utilization of the estimator; any means for determining the blood pressure waveform within the pulmonary artery, including sensor-tipped needles and ultrasonic techniques among others, will equivalently suffice.

According to the preferred implementation, the neural network 14 is provided with four fully connected layers—an input layer 17 of 23 nodes, two hidden layers 18, 19 of 12 nodes each and a single node output layer 20. A single heartbeat of pressure waveform, sensed through the catheter 15 and acquired by the data acquisition board 12 and software, is isolated, end disastoli-to-end diastoli, and parsed into 11 samples by the preprocessing function. The preprocessing function also determines the first derivative of the blood pressure waveform and provides 11 samples in time-correspondence to the 11 blood pressure samples. These 22 samples and one data input representative of end diastoli-to-end diastoli heartbeat duration, in milliseconds, are then fed as a raw input vector into the input layer 17 of the neural network 14. The resulting output of the neural network 14 is the estimate of the pulmonary wedge pressure corresponding to the sampled heartbeat.

As stated herein above, a flow-directed catheter 15 is particularly suited for obtaining the pulmonary artery pressure readings. This is because in training the neural network 14, as discussed further herein, it is necessary to actually occlude the pulmonary artery 21, which necessitates inflation of a catheter balloon 22. Utilizing the same type of device to obtain the pressure reading in practice, although not absolutely required, will serve to help prevent the introduction of anomalies into the system.

In training or utilization of the wedge pressure estimator, the pulmonary artery catheter 15 is first placed in the patient. As is known to those of ordinary skill in the art, any of a plurality of sites may be chosen for catheterization of the patient. Specifically, the flow-directed catheter may be inserted in the jugular, subclavian, femoral or anticubital facies regions. Catheterization in the femoral region presents an increased risk of thrombous formation and catheterization in the subclavian region presents the remote possibility of puncturing a lung during insertion. Catheterization in the anticubital facies region necessitates immobilization of the patient's arm and impedes utilization of the arm for other purposes such as drug administration. It is therefore preferred that catheterization take place in the jugular region whereby these and other possible complications, such as venospasm, are avoided.

As is known in the art, the chosen insertion point is dissected to the vein which is lifted from the wound by distal and proximal ties. An incision is then made into the vein and held open with a vein holder as the flow-directed catheter is inserted. Assuming insertion through the jugular, the polyurethane balloon 22 is inflated when the tip of the catheter 15 is in the superior vena cava 23. The flow-directed catheter 15 is then guided into the right atrium 24, through the tricuspid valve 25 and into the right ventrical 26. It is important that the polyurethane balloon be soft in order to prevent tachycardia when the tip of the catheter 15 touches the right ventricular wall. Finally, the flow-directed catheter 15 is passed through the pulmonic valve 27 and into the pulmonary artery 21 where it may remain for up to several days. The insertion wound is then dressed; as the flow-directed catheter 15 is almost always used in acutely ill patients, insertion of the catheter 15 and dressing of the wound requires the utmost care and sterile conditions.

To train the neural network 14 for implementation of the present invention, training data comprising pulmonary artery blood pressure waveform data and occlusion obtained wedge pressure data must be gathered. Specifically, the network training data is acquired, using the data acquisition board 12 and software, by capturing 10 to 20 heartbeats of pulmonary artery blood pressure waveform and then occluding the pulmonary artery 21 to immediately capture the corresponding pulmonary wedge pressure. This process may be repeated several times in a single patient during the ordinary course of treatment under the conventional method. Data from many patients, each undergoing ordinary and conventional treatment, is then preprocessed and pooled to form the training data set. As is well known to those of ordinary skill in the art, the back-propagation neural network 14 is trained by presenting an input data vector to the network and then comparing the generated output with the desired, or known, output which in this case is the occlusion obtained wedge pressure. An algorithm specific set of error equations is then utilized to adjust the internal coefficients, or weights, of the neural network in order to force the network to converge to desired outputs. Once the developer is satisfied that the network 14 is fully trained, the coefficients are frozen and the system is deemed ready for operation.

In operation, the patient is catheterized 28 as in the training situation. In practice, however, the pulmonary wedge pressure is estimated directly from the pulmonary artery blood pressure waveform, obviating the need to inflate the catheter balloon 22. The pulmonary artery blood pressure waveform is acquired 29 and then preprocessed 30 for presentation to the neural network. The neural network then directly estimates 31 the pulmonary wedge pressure on a beat-to-beat basis. Because the wedge pressure can be calculated for each and every heartbeat of blood pressure data, the dynamics of the pulmonary wedge pressure are readily obtained and are obtained with minimal risk to the patient.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and the claims drawn hereto. For example, the preferred embodiment of the present invention has been described in as utilizing a fully connected neural network. In practice, however, it is found that the cross co-variance matrix of the input data shows a strong interdependence in the input data. As a result, it is to be expected that many standard pruning algorithms should be successful in eliminating many weights and connections from the trained network. To this end, implementations utilizing concatenated networks are to be considered fully within the scope of the present invention.

As yet another example, the present invention can be extended to provide an estimation of the pulmonary capillary pressure—an important indication of a patient's fluid balance. In this case, the estimation of left atrial pressure is utilized in the well-known Gaar's equation to arrive at the pulmonary capillary pressure. In any case, because the scope of the present invention is much broader than any particular embodiment, the foregoing detailed description should not be construed as a limitation of the present invention, which is limited only by the claims appended hereto.

What is claimed is:

1. A medical device for estimation of pulmonary wedge pressure, comprising:

a non-occluding pulmonary artery pressure acquisition device, said pressure acquisition device being adapted for sensing pulmonary artery blood pressure; and a signal processing device, in communication with said pressure acquisition device, said signal processing device being adapted for estimating pulmonary wedge pressure based upon sensed pulmonary artery blood pressure.

2. The medical device as recited in claim 1, wherein said signal processing device comprises:

a neural network trained to estimate pulmonary wedge pressure from an input vector comprising pulmonary artery blood pressure data sensed by said pressure acquisition device.

3. The medical device as recited in claim 2, wherein said neural network is trained to estimate pulmonary wedge pressure from an input vector further comprising the first derivative of pulmonary artery blood pressure data sensed by said pressure acquisition device.

4. The medical device as recited in claim 2, wherein said neural network is a backward error propagation neural network.

5. The medical device as recited in claim 2, wherein said pressure acquisition device comprises a flow-directed catheter.

6. The medical device as recited in claim 5, wherein said pressure acquisition device further comprises an analog-to-digital data acquisition board, said data acquisition board being adapted for collecting blood pressure data.

7. The medical device as recited in claim 5, wherein said signal processing device further comprises a preprocessor, said preprocessor being adapted for parsing blood pressure data collected by said data acquisition board.

8. A medical device for estimating pulmonary wedge pressure, said medical device being developed through the steps of:

collecting a set of training data inputs, each said input comprising a pulmonary artery wedge pressure measurement and at least one corresponding pre-occlusion heartbeat-duration of pulmonary artery blood pressure data;

training a neural network, utilizing said set of training data inputs, to estimate pulmonary artery wedge pressure based upon non-occluded pulmonary artery blood pressure; and implementing said neural network within said medical device.

9. A method for estimation of pulmonary artery wedge pressure, comprising the steps of:

obtaining a non-occluded pulmonary artery blood pressure waveform; and converting said blood pressure waveform into beat-to-beat pulmonary wedge pressure.

* * * * *